US007977054B2

(12) United States Patent
Johnson, Jr. et al.

(10) Patent No.: US 7,977,054 B2
(45) Date of Patent: Jul. 12, 2011

(54) SINGLE WALLED CARBON NANOTUBES FUNCTIONALLY ADSORBED TO BIOPOLYMERS FOR USE AS CHEMICAL SENSORS

(75) Inventors: Alan T. Johnson, Jr., Philadelphia, PA (US); Alan Gelperin, Princeton, NJ (US); Cristian Staii, Madison, WI (US)

(73) Assignees: The Trustees of the University of Pennsylvania, Philadelphia, PA (US); Monell Chemical Senses Center, Philadelphia, PA (US)

( * ) Notice: Subject to any disclaimer, the term of this patent is extended or adjusted under 35 U.S.C. 154(b) by 137 days.

(21) Appl. No.: 11/910,070

(22) PCT Filed: Mar. 29, 2006

(86) PCT No.: PCT/US2006/012005
§ 371 (c)(1),
(2), (4) Date: Mar. 13, 2008

(87) PCT Pub. No.: WO2006/110347
PCT Pub. Date: Oct. 19, 2006

(65) Prior Publication Data
US 2008/0274912 A1 Nov. 6, 2008

Related U.S. Application Data

(60) Provisional application No. 60/666,232, filed on Mar. 29, 2005, provisional application No. 60/710,708, filed on Aug. 22, 2005.

(51) Int. Cl.
*C12Q 1/68* (2006.01)
*G01N 27/26* (2006.01)
*C12P 19/34* (2006.01)
*C07H 21/02* (2006.01)
*C07H 21/04* (2006.01)

(52) U.S. Cl. ..... 435/6; 204/403.01; 435/91.1; 536/23.1; 536/24.3

(58) Field of Classification Search ............. 435/6, 91.1; 536/23.1, 24.3; 424/1.13; 436/501; 204/403.01
See application file for complete search history.

(56) References Cited

U.S. PATENT DOCUMENTS

| | | | |
|---|---|---|---|
| 4,563,893 | A | 1/1986 | Tanyolac et al. |
| 6,649,403 | B1 | 11/2003 | McDevitt et al. |
| 6,905,655 | B2 | 6/2005 | Gabriel et al. |
| 7,129,554 | B2 | 10/2006 | Lieber et al. |
| 2004/0101851 | A1* | 5/2004 | White et al. ............ 435/6 |
| 2004/0200734 | A1* | 10/2004 | Co et al. ............ 205/777.5 |
| 2006/0145194 | A1 | 7/2006 | Barron et al. |

OTHER PUBLICATIONS

Chopra, S. et al., Appl. Phys. Lett., vol. 83, No. 11, p. 2280 (2003).*
Keren, K. et al., Science, vol. 302, pp. 1380-1382 (2003).*
Barone, P.W. et al., "Near-infrared optical sensors based on single-walled carbon nanotubes," Nat. Mater., 2005, 4, 86-92.
Berendsen, H.J. et al., "Molecular dynamics with coupling to an external bath," J. Chem. Phys., 1984, 81, 3684-3690.
Bradley, K. et al., "Charge Transfer from Ammonia Physisorbed on Nanotubes," Phys. Rev. Lett., Nov. 2003, 91(21), 218301-1 to 218301-4.
Bradley, K. et al., "Short-channel effects in contact-passivated nanotube chemical sensors," Appl. Phys. Lett., 2003, 3821-3823.
Breaker, R.R., "Natural and engineered nucleic acids as tools to explore biology," Nature, 2004, 432, 838-845.
Chen, R.J. et al., "An Investigation of the Mechanisms of Electronic Sensing of Protein Adsorption on Carbon Nanotube Devices," J. Am. Chem. Soc., 2004, 126, 1563-1568.
Chen, R.J. et al., "Noncovalent functionalization of carbon nanotubes for highly specific electronic biosensors," Proc. Natl. Acad. Sci. USA, 2003, 100, 4984-4989.
Chopra, S. et al., "Selective gas detection using a carbon nanotube sensor," Appl. Phys. Lett., 2003, 83, 2280-2282.
D'Amico, A. and Di Natale, C., "Electronic Nose Applications," Nose Summer School, Lloret de Mar, Oct. 2-6, 2000, University of Roma Tor Vergata.
Freitag, M. et al., "Role of Single Defects in Electronic Transport through Carbon Nanotube Field-Effect Transistors," Phys. Rev. Lett., 2002, 89(21), 216801.
Gao, H. et al., "Stimulation of DNA-Nanotube Interactions," Annu. Rev. Mater. Res., 2004, 34, 123-150.
Gouma, P. et al., "Novel Materials and Applications of Electronic Noses and Tongues," MRS Bulletin, Oct. 2004, 697-702.
Hahm, J.I. et al., "Direct Ultrasensitive Electrical Detection of DNA and DNA Sequence Variations Using Nanowire Nanosensors," 2004, 4, 51-54.
Keren, K. et al., "DNA-Templated Carbon Nanotube Field-Effect Transistor," Science, Nov. 21, 2003, 302, 1380-1382.
Kong, J. et al., "Nanotube Molecular Wires as Chemical Sensors," Science, 2000, 287, 622-625.
Martel, R. et al., "Single- and Multi-wall carbon nanotube field-effect transistors," Applied Physics Letters, Oct. 26, 1998, 73(17), 2447-2449.
Nakao, H. et al., "Transfer-Printing of Highly Aligned DNA Nanowires," J. Am. Chem. Soc., 2003, 125(24), 7162-7163.
Novak, J.P. et al., "Nerve agent detection using networks of single-walled carbon nanotubes," Appl. Phys. Lett., 2003, 83, 4026-4028.
Parrinello, M. et al., "Polymorphic transitions in single crystals: a new molecular dynamics method," J. Appl. Phys., 1981, 52, 7182-7190.
Patel, D.J. et al., "Structure, recognition and adaptive binding in RNA aptamer complexes," J. Mol. Biol., 1997, 272, 645-664.
Pengfei Qi et al., "Toward Large Arrays of Multiplex Functionalized Carbon Nanotube sensors for Highly Sensitive and Selective Molecular Detection," Nano Lett., 2003, 3, 347-351.

(Continued)

*Primary Examiner* — Jane Zara
(74) *Attorney, Agent, or Firm* — Woodcock Washburn, LLP (57) ABSTRACT

Chemical field effect sensors comprising nanotube field effect devices having biopolymers such as single stranded DNA functionally adsorbed to the nanotubes are provided. Also included are arrays comprising the sensors and methods of using the devices to detect volatile compounds.

26 Claims, 5 Drawing Sheets

OTHER PUBLICATIONS

Radosavljevic, M. et al., "Nonvolatile Molecular Memory Elements Based on Ambipolar Nanotube Field Effect Transistors," Nano Lett., 2002, 2(7), 761-764.

Sergi, M. et al., "Proteins, recognition networks and developing interfaces for macromolecular biosensing," J. Mol. Recog., 2004, 17, 198-208.

Sirdeshmuhk, R. et al., "Biological Functionalization of Carbon Nanotubes," Mat. Res. Soc. Symp. Proc., vol. 823 © 2004, Materials Research Society, W4.1.1-W4.1.6.

Snow, E.S. et al., "Chemical Detection with a Single-Walled Carbon Nanotube Capacitor," Science, 2005, 307, 1942-1945.

Staii, C. et al., "DNA-Decorated Carbon Nanotubes for Chemical Sensing," Nano Letters, 2005, 5(9), 1774-1778.

Staii, C. et al., "High Frequency Scanning Gate Microscopy and Local Memory Effect of Carbon Nanotube Transistors," Nano Lett., 2005, 5(5), 893-896.

Valentini, L. et al., "Sensors for sub-ppm $NO_2$ gas detection based on carbon nanotube thin films," Appl. Phys. Lett., 2003, 82, 961-963.

Wang, W. et al., "Label-free detection of small-molecule-protein interactions by using nanowire nanosensors," Proc. Natl. Acad. Sci. USA, 2005, 102, 3208-3212.

Williams, K.A. et al., "Covalently Functionalized Nanotubes as Nanometer-Sized Probes in Chemistry and Biology," Nature, 2002, 420, 761.

Wong, S.S. et al., "Carbon nanotubes with DNA recognition," Nature, 1998, 394, 52-55.

Zhang, D. et al., "Detection of $NO_2$ down to ppb Levels Using Individual and Multiple $In_2O_3$ Nanwire Devices," Nano Lett., 2004, 4, 1919-1924.

Zheng, M. et al., "DNA-assisted dispersion and separation of carbon nanotubes," Nature Mater., 2003, 2, 338-342.

\* cited by examiner

SINGLE WALLED CARBON NANOTUBES FUNCTIONALLY ADSORBED TO BIOPOLYMERS FOR USE AS CHEMICAL SENSORS

CROSS-REFERENCE TO RELATED APPLICATIONS

This application is the National Stage of International Application No. PCT/US2006/012005 filed Mar. 29, 2006, which claims the benefit of U.S. Provisional Application No. 60/666,232, filed Mar. 29, 2005 and U.S. Provisional Application No. 60/710,708, filed Aug. 22, 2005, the disclosures of which are incorporated herein by reference in their entireties.

GOVERNMENT SUPPORT

Research leading to the disclosed inventions was funded, in part, by the United States Department of Energy, Grant No. DE-FG02-98ER45701, and from the Laboratory for Research on the Structure of Matter, National Science Foundation, Grant No. NSF DMR00-79909. Accordingly, the United States government may have certain rights in the inventions described herein.

FIELD OF THE INVENTION

This invention relates to the field of chemical sensors. The invention also relates to the field of field-effect devices and sensor arrays. The field of the invention also pertains to using sensors both individually, in combination, and in array fashion for detecting compounds.

BACKGROUND OF THE INVENTION

The concept of an "electronic nose" has been an active area of research for some decades. Researchers have been trying to provide such a device e.g., by attempting to couple an array of chemical odor sensors with a pattern-recognition system. NASA, for instance, has been trying to develop such a nose to detect the presence of gases such as ammonia that may be poisonous to astronauts. Ammonia is integral to life on the space station because it carries heat originating inside the station through pipes outside to space. However, ammonia is poisonous and a leak must be detected quickly and stopped. Humans are only capable of detecting ammonia at about 50 ppm, although it can be dangerous at a concentration of only a few parts per million. A suitable sensor, or electronic nose capable of detecting ammonia at such low concentrations is needed.

Considerable interest has been generated by the Department of Homeland Security about the use of electronic devices in detecting volatile compounds to prevent explosive, chemical, or biological attacks. Screening methods developed to detect explosive or toxic chemicals that may be carried through an airport or seaport are, in many ways, a first line of defense in protecting against such attacks. Such methods currently include laboratory analyses of suspected drugs, drug-sniffing dogs, and the ubiquitous X-ray machine. For most laboratory methods to be performed, a great deal of time must be spent in preparing samples for analysis. Small, portable devices would likely reduce the time needed to detect potential threats Previous attempts at making electronic noses generally follow the same principle, coupling an array of chemical detectors with pattern recognition systems. However, they differ with respect to the selection of sensors. Common sensor designs include mass transducing, such as quartz microbalance, surface acoustic wave transducers, chemoresistors, and hybrids of such. In any event, it is greatly desired that sensors used for electronic noses and molecular detection exist and function on a very compact—even molecular—scale and exhibit very good electronic properties.

Since their discovery, carbon nanotubes have stimulated widespread scientific research due to their promising electronic and mechanical properties. Their electronic properties, for instance those exhibited in semiconducting nanotubes, suggest conductivity characteristics that change as a result of local electrical field strength. Martel, et al., "Single and Multi-Wall Nanotube Field Effect Transistors," Applied Physics Letters, Volume 73, Number 17, 26 Oct., 1998, have constructed molecular structures that exhibit field-effect transistor (FET) characteristics using nanotubes that exhibit variable electrical conductance attributes. An FET, which is known to the art per se, may be described as a current device in which current flows in a channel between two electrodes where the effective resistance of the channel may be controlled using a gate electrode which alters the strength of the electric field in the channel.

The use of single walled carbon nanotubes (SWNT) as chemical sensors has been explored in the works of Chen R J, et. al., (2004) J. Am. Chem. Soc. 126:1563-8; and, Bradley K, et. al. (2003) Phys. Rev. Lett., 91:218301. The one-dimensional carbon cage structure of semiconducting SWNTs makes their physical properties exquisitely sensitive to variations in the surrounding electrostatic environment, whether the SWNTs are suspended in liquid or incorporated in to the FET circuits on a substrate. (Kong J et al. (2000) Science 287"622-5; Freitage M et al. (2002) Phys Rev Lett 89 art. No. 216801; and, Pengfei Q F et al. (2003) Nano Lett. 3:347-51). Bare and polymer-coated SWNTs have been reported to be sensitive to various gases, but SWNTs functionalized with biomolecular complexes are believed to hold the greatest promise as molecular probes and sensors for chemicals that do not interact, or interact only weakly with bare carbon nanotubes (Chopra S et al. Appl. Phys. Lett. (2003) 83:2280-2; Li J et al. (2003) Nano Lett. 3:929-33; Novak J P et al (2003) Appl. Phys. Lett. 83:4026-8; Valentini L et al. (2003) Appl. Phys. Lett. 82:961-3; Bradley K et al. (2003) Appl. Phys. Lett. 83:3821-3; Snow E S et al. (2005) Science 307:1942-5; Wong S S et al. (1998) Nature 394:52-5; Williams K A et al. (2002) Nature 420:761; Chen R J et al. (2003) Proc. Natl. Acad. Sci. USA 100:4984-9; and, Barone P W et al. (2005) Nat. Mater. 4:86-92.)

Derivatized SWNT-FETs are attractive as electronic read-out molecular sensors due to their high sensitivity, fast response time, and compatibility with dense array fabrication (Pegfei Q F et al. 2003). Derivatized semiconductor nanowires have similar performance advantages, and recent work indicates that they hold promise as gas and liquid-phase sensors (Zhang D et al. (2004) Nano Lett. 4:1919-24; Hahm J I et al. (2004) 4:51-4; and, Wang W et al. (2005) Proc. Natl. Acad. Sci. USA 102:3208-12.)

It is desirable to functionalize SWNT sensors in a way to achieve robust, reproducible decoration, with concomitant molecular flexibility to provide sensitivity to a wide spectrum of analytes. To avoid degrading the high quality electronic properties of the SWNT-FET, it is also desirable that the functionalization be non-covalent.

Nucleic acids are intriguing candidates for use as in the molecular targeting layer of SWNT-FETs. Nucleic acids are advantageous in that they can be engineered for affinity to a wide spectrum of targets, including small molecules, proteins, and other nucleic acids (Patel D J et al. (1997) J. Mol.

Biol. 272:645-64; and, Breaker R R (2004) Nature 432:838-45). Single-stranded DNA (ssDNA) labeled with fluorescent tags has shown promise as a sensor of volatile compounds. In U.S. Patent Application Publication No. 2004/0101851 A1, White and Kauer discuss that fluorescence from tagged ssDNA changes when a bulk layer of a molecule is exposed to odor samples. In the White and Kauer system, dyes interclated within the DNA change fluorescence upon exposure to the odor compound relative to the intensity observed upon exposure to clean air controls. ssDNA possesses the additional advantage of having a high affinity for SWNTs due to a favorable pi-pi stacking interaction, and thus can facilitate functionalization of the carbon nanotube (Zheng M et al. (2003) Nature Mater. 2:338-42). Moreover, because different ssDNA strands show different response characteristics, the unique chemical structures of specific ssDNA oligomers grant the sensors made from the tagged DNA customizable binding properties.

A significant advance in the art would be to provide chemical sensors that are compact and capable of detecting volatile compounds with all-electronic readout. It is desirable that such sensors be capable of easy modification, in order to provide a wider array of potential sensitivities as well as to be able to enhance the sensitivity to known analytes. Similarly, as the sensors currently available suffer from the major drawback of irreversible adsorption, it is desirable to provide sensors that are capable of self-regeneration in order to prolong the usefulness of the device and save on cost. Also needed are methods of detecting such volatile compounds using a device comprising individual sensors or arrays made of compact chemical sensors.

SUMMARY OF THE INVENTION

Electronic noses and other forms of molecular sensors are provided by this invention and are useful in a number of areas. These include determining the freshness of food, identification of spilled chemicals, and diagnosis of disease states through sampling of head spaces of patient odors, sampling of tissues, and body fluids or the like. Other uses are also apparent, including waste water analysis, determination of explosives, evaluation of the contents of containers and vehicles. However, effective, compact, rapid, reliable and controllable sensors are required for these and other sensing purposes. These objectives are attained through the employment of the aspects of the present invention. The wide variability of biopolymers which may form a part of the sensors of the present invention gives rise to huge diversity in the nature of species which may be detected thereby.

The present invention features chemical sensors comprising a substrate, an insulating layer, and source and drain electrodes on the insulating layer. In contact with each of the source and drain electrodes is at least one nanotube functionally adsorbed to a biopolymer. The nanotubes used can be semiconducting in some embodiments. In some embodiments, the substrate can be semiconducting. Also featured are chemical sensors adapted to have a gate voltage applied to the substrate and a bias voltage applied between the source and drain electrodes, the nanotube being capable of conducting current between the source and drain electrodes under some conditions of electric field strength local to the nanotube.

The biopolymer can be a polynucleotide, and preferably is single stranded DNA. The biopolymer is capable of interacting with at least one target molecular species to affect the electric field local to the nanotube in some exemplary embodiments. Altered current flow in the nanotube accompanies interaction of the molecular species to be detected with the biopolymer. In many cases, the amount or concentration of target molecular species may be quantified through use of the sensors and methods of this invention.

Also described herein are methods of using a chemical sensor comprising a substrate; an insulating layer; source and drain electrodes on the insulating layer; and, in contact with each of the source and drain electrodes, at least one nanotube functionally adsorbed to a biopolymer; said method comprising contacting said sensor with an atmosphere sample and detecting the presence or absence of a volatile compound. Chemical sensor arrays comprising a plurality of the sensors described herein are also disclosed.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 3 shows the change in sensor current upon odor exposure. Currents are normalized to $I_o$, the value when exposed to air (no odor). (a) Bare SWNT-FET does not respond to methanol vapor (black points). The same device coated with ssDNA having SEQ ID NO:2 shows clear responses to methanol (grey points). (b) A second bare device responds to TMA (black points) but after application of Seq. 2, the response is tripled (grey points). (c) The sensor response to propionic acid (black points) differs in sign and magnitude from the response to methanol (grey points). Light grey data points represent the current baseline (no odor). $V_B$=100 mV and $V_G$=0 V for all data sets.

FIG. 4 shows (a) Change in the device current when sarin-simulant DMMP is applied to SWNT-FETs before and after ss-DNA functionalization. (b) Sensor response to DNT.

DETAILED DESCRIPTION OF ILLUSTRATIVE EMBODIMENTS

The chemical sensors described herein function as high sensitivity gas sensors that exhibit conductivity changes in response to odor application. SWNTs may be arranged into devices that exhibit characteristics similar to all semiconductor field effect transistors (FETs). Such a SWNT-based device may be called a SWNT-FET device. SWNT-FET devices lacking biopolymers on their nanotubes do not exhibit a conductivity response to many volatile gases. In contrast, embodiments of the chemical sensors, or field effect sensors, described herein are responsive to such gases. The responses differ in sign and magnitude for different odors, and the odor response characteristics may depends on the physical characteristics of the biopolymer used, such as the base sequence of a ssDNA polynucleotide. Volatile compounds that do not exhibit a conductivity response in single semiconducting SWNT devices may exhibit conductivity responses in devices with multiple SWNTs.

Without intending to be limited to any particular mechanism or theory of operation, it is believed that the electrical conductivity of a SWNT FET device is sensitive to charged species bound near the nanotube sidewall because such changed species affect the local electric field near the conduction channel formed by the nanotube. However, the nanotube sidewall typically becomes functionalized before SWNT FETs can be useful chemical sensors in accordance with this invention. Functionalization allows a desired molecular species to be preferentially and specifically bound to the nanotube. Functionalization thus enhances the sensitivity of the SWNT detector as well as the potential range of molecules that can be detected by the SWNT-FET. In accordance with the invention, many modes of functionalization may be employed, however, it is preferable to use a biopolymer or biopolymers such as a polynucleotide or polypeptide, although other biopolymers such as carbohydrates can be used. Particularly preferred polynucleotides are capable of adsorbing to the SWNT through the pi-pi stacking effects. In preferred embodiments, the polynucleotides such as ssDNA are reversibly adsorbed to the SWNT to facilitate regeneration of the sensor. Particularly preferred polynucleotides display secondary structures that specifically bind to odor molecules. Most preferred is ssDNA that adsorbs on the SWNT and produces a positive electrostatic potential at the surface of the SWNT.

The chemical sensors described presently can be used as the sensor elements in an array of sensors, each with an individualized response characteristic, coupled to an advanced pattern recognition data processing system. Biopolymers provide an extensive library of compounds for the present sensors. Many are expected to have a binding affinity to SWNT through a pi-pi stacking interaction. Moreover, a variety of methods, such as directed evolution, may be used to create DNA or RNA molecules designed to bind other target molecules, including nucleic acids, proteins, small organic compounds, or even entire organisms. Thus, the chemical sensors of the present invention may be produced with sensitivity to a large variety of compounds.

The present disclosure describes chemical sensors comprising a substrate that may be semiconducting in some embodiments; an insulating layer; source and drain electrodes on the insulating layer; and, in contact with each of the source and drain electrodes, at least one nanotube functionally adsorbed to a biopolymer. In some embodiments, the sensor is adapted to have a gate voltage applied to the substrate and a bias voltage applied between the source and drain electrodes. The nanotube is then capable of conducting current between the source and drain electrodes under some conditions of electric field strength local to the nanotube. The nanotube may be semiconducting.

Figure 1A:
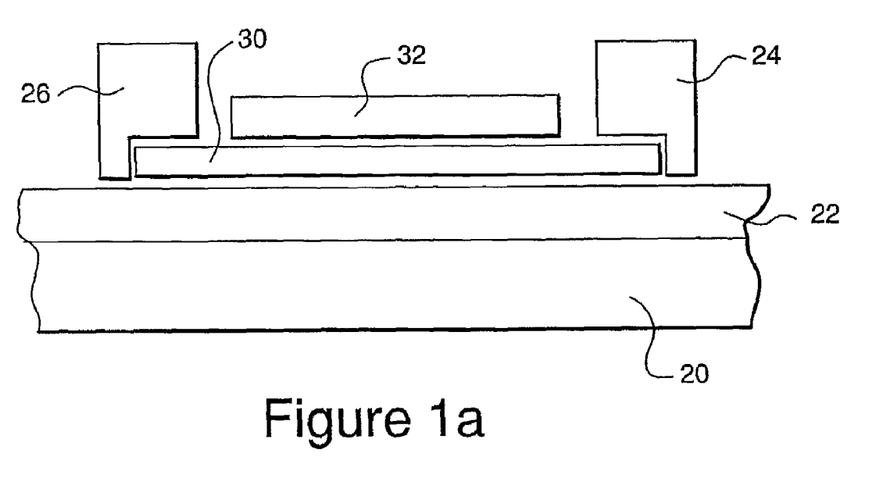
FIG. 1a is a schematic representation of a chemical sensor showing an insulating layer resting upon a semiconducting substrate, with carbon nanotube upon the semiconducting substrate between source and drain electrodes. ssDNA is shown on top of the carbon nanotube.
Figure 1B:
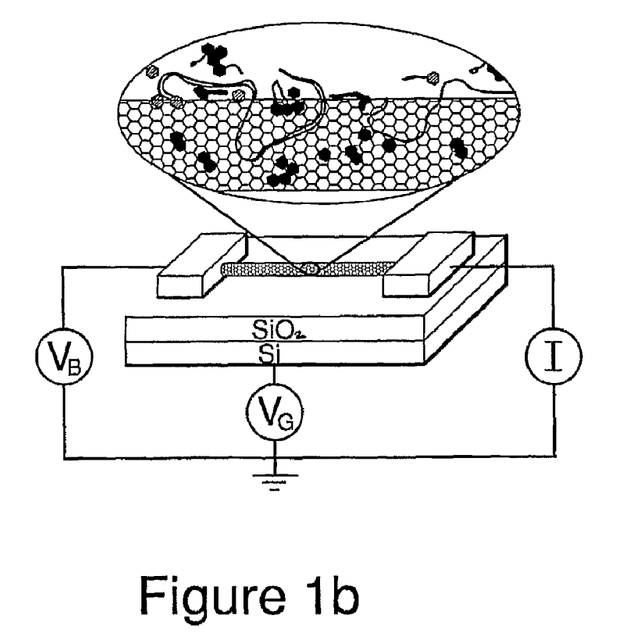
FIG. 1b shows a cartoon representation of the sensor, with an exploded view of polynucleotides functionalized to the carbon nanotube.

FIG. 1 depicts a schematic of a chemical sensor that may be used in some embodiments described herein. An insulating layer 22 rests upon a semiconducting substrate 20. The insulating layer 22 may be silicon dioxide or other electrically insulative material known in the art, while the semiconducting layer 20 acts as a back gate. Any semiconducting or conducting material known to those of skill in the art may be used to comprise the back gate. Such materials, including compounds of the materials, may include, but not be limited to, silicon, germanium, gallium, indium, aluminum, gold, copper, diamond, nitride, arsenide and carbide. Source 26 and drain 24 electrodes may be composed of an electrically conductive metal, such as gold, silver, aluminum, chromium, titanium, or copper. The use of an appropriately doped semiconductor material is also contemplated for electrodes 24 and 26. A carbon anotube 30 rests between the source 26 and the drain 24 electrodes and is in contact with each. A polynucleotide such as ssDNA 32 is functionalized to the carbon nanotube 30.

Placing biopolymers on the nanotubes of the present chemical sensors gives the device gas-sensing functionality that utilizes individualized binding properties. The binding affinity of biopolymers, such as ssDNA for example, implies that there will be strong binding between the SWNT and the biopolymer. Molecules or volatile compounds bound by the biopolymers on the SWNT will be brought into close contact with the field effect sensor. This affords great compatibility with modern microfabrication techniques, the convenience of electronic readout, small footprint, and ease of fabrication. Useful biopolymers compatible with the present invention include, but are not limited to, polynucleotides such as DNA and RNA, polypeptides, nucleic acid-polypeptide complexes, carbohydrates, aptamers, ribozymes, and all homologs, analogs, conjugates, or derivatives thereof, as well as mixtures thereof. The term "polynucleotide," generally refers to any polyribonucleotide or polydeoxribonucleotide, which may be unmodified RNA or DNA or modified RNA or DNA. Polynucleotides include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide encompasses triple-stranded regions comprising RNA or DNA or both RNA and DNA. The term polynucleotide also includes DNAs or RNAs containing one or more modified bases and DNAs or RNAs with backbones modified for stability or for other reasons. Modified bases include, for example, tritylated bases and unusual bases such as inosine. A variety of modifications can be made to DNA and RNA; thus, polynucleotide embraces chemically, enzymatically or metabolically modified forms of polynucleotides as typically found in nature, as well as the chemical forms of DNA and RNA characteristic of viruses and cells. Polynucleotide, as used herein, also embraces relatively short nucleic acid chains, often referred to as oligonucleotides. In preferred embodiments of the invention, single stranded DNA is used. These biopolymers provide a comprehensive library of compounds, each with specific binding characteristics.

The biopolymers can be attached by reacting a solution of DNA with other biopolymers, such as RNA, peptides, etc., before application of a derivatized DNA to the nanotube. In other embodiments, a bare chemical sensor (a sensor having no biopolymer on a nanotube) can first be treated with a given DNA oligomer and then a second biopolymer solution applied to the DNA-decorated sensor.

The biopolymers act both as a linker to the SWNT and a binding site for the volatile compound or odor analyte. These two tasks may be performed by using two separate molecules. For example, the ssDNA could act as a linker module for a separate protein molecule that acts as a targeting module. The targeting module in turn is used to attract specific compounds to be measured as suggested by M. Sergi, et. al., (2004) J. Mol. Recog. 17:198-208. Aptamers may be developed for their affinity for specific proteins, and these molecules should retain their designed binding specificity even when associated with a SWNT. Along with the gas phase detection described herein and in the examples below, the chemical sensors of the present invention may be compatible with liquid phase detection.

Nucleic acid hybridization may also be measured using some embodiments. A SWNT forming a part of a sensor of this invention may be decorated with ssDNA, e.g. having the ssDNA applied to the surface of the SWNT. A sample may then be brought into contact with the sensor that contains a nucleic acid or other molecule for which the binding affinity with the superficial DNA is desired to be determined. Operation of the sensor will, in many cases, give rise to information concerning this interaction and the binding affinity may, thus, be determined.

Single stranded DNA decorated SWNTs may be used as electrochemical electrodes. First, a ssDNA strand known or expected to have affinity for an odor analyte of interest is selected. There may be a bundle of SWNTs decorated with ssDNA exposed to a liquid containing the analyte. If the analyte is bound by the SWNT-ssDNA electrode, standard electrochemical measurement (cyclic voltammetry) is expected to show a current flow into the liquid at a voltage that is characteristic of the analyte.

Embodiments of the present invention also include methods of using a chemical sensor comprising a substrate that may be semiconducting in some embodiments; an insulating layer; source and drain electrodes on the insulating layer; and, in contact with each of the source and drain electrodes, at least one nanotube having biopolymer thereupon; said method comprising contacting said sensor with an atmosphere sample and detecting the presence or absence of a volatile compound. Volatile compounds, as used herein, may be considered as compounds vaporized in the atmosphere. The present methods and devices also detect an odor analyte which is considered a sample of the atmosphere to be tested or analyzed.

Chemical sensor arrays are also provided by the present invention. A sensor array comprises a plurality of sensors in accordance with the sensors described above. The arrays may have different sensors or sets of sensors that are sensitive to a different molecule, molecular family, or genus. The arrays also comprise a data processing system. The system may also comprise a pattern recognition system or other control system.

In one embodiment of the invention, pluralities of field-effect devices, or sensors, are employed to discriminate among different target molecules. A number of different sensors are prepared having SWNTs forming a part of them in accordance with this invention, where the SWNTs of the different sensors have different biopolymers thereupon. A single sample of a sensor may comprise an individual field effect device or may comprise dozens or hundreds of identical field effect devices, it being understood that redundancy gives rise to improved accuracy. In any event, a plurality of different sensors is arrayed in a single apparatus with an appropriate controller in electrical communication therewith. Contacting the array with an analyte causes differential responses in the different sensors with the respective currents being evaluated by the controller. The controller is in communication with computational, evaluative, or other display means in order to reflect the interactions of the sensors with the analyte. Through comparison of the results of the analysis either with prior analysis or with expected values, knowledge of the nature of the analyte may be had.

In view of the foregoing, it is apparent that different individual sensors and assemblages or arrays of either the same or different sensors can be used for predefined purposes. Thus, expected responses of sensors in accordance with this invention may be compared with responses from test gasses, liquids, tissues, head spaces, environments samples and other test samples to determine their contents either qualitatively or with identical determination of contents. Quantification may also ensue.

EXAMPLE 1

Preparation of SWNT-FETs

SWNTs were grown by catalytic chemical vapor deposition (CVD) on a $SiO_2$/Si substrate. FET circuits were fabricated with Cr/Au source and drain electrodes patterned using electron beam lithography and the degenerately doped silicon substrate used as a backgate (FIGS. 1a and b) (Radosavljevic M et al. (2002) Nano Lett. 2:761-4). For each device, source-drain current I was measured as a function of bias voltage $V_B$ and gate voltage $V_G$ under ambient laboratory conditions. Circuits consisting of individual p-type semiconducting nanotubes, where the carriers are positively charged holes, were selected by using only devices that showed a strong decrease in $I(V_G)$ for positive $V_G$ (ON/OFF ratio exceeding 1000).

ssDNA was adsorbed to the SWNT. The ssDNA functionally adsorbed to the SWNT had either of the following sequences, as described in U.S. Patent Application Publication No. 2004/0101851:

5' GAGTCTGTGGAGGAGGTAGTC 3',    (SEQ ID NO: 1)

or,

5' CTTCTGTCTTGATGTTTGTCAAAC 3'.    (SEQ ID NO: 2)

Single stranded oligonucleotides were obtained from Invitrogen (Carlsbad, Calif.) and diluted in distilled water to make a stock solution of 658 µg/ml (SEQ ID NO: 1) or 728 µg/ml (SEQ ID NO: 2). After odor responses of the bare SWNT-FET device were measured, a 500 µm diameter drop of ssDNA solution was applied to the device for 45 min, and then dried under a nitrogen stream. About 25 devices from two different SWNT growth runs were selected for detailed analysis and treated with ssDNA for the experiments.

Figure 2A:
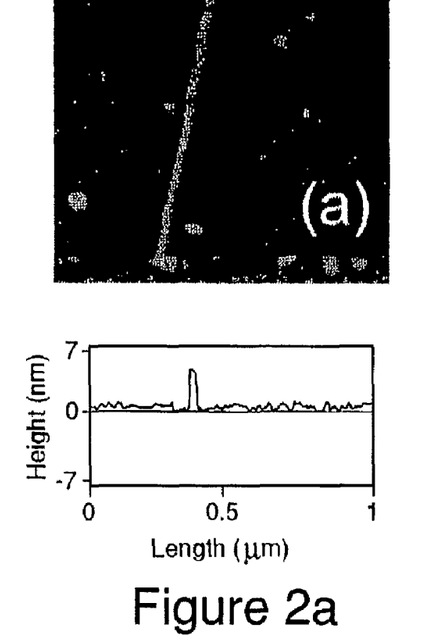
FIGS. 2(a) and (b) show AFM images (1 µm×1 µm, z-range 10 nm) and line scans of the same SWNT before (a) and after (b) functionalization with ssDNA. The measured diameter of the bare SWNT is 5.4±0.1 nm, while after application of ssDNA its diameter is 7.2±0.2 nm. The increase in surface roughness in (b) is attributed to non-specific binding of ssDNA to the $SiO_2$ substrate. (c) Current (I) versus backgate voltage ($V_G$) characteristic of a bare SWNT-FET sensor (blue), the same device after functionalization with ssDNA sequence 1 and exposed to air (grey), the same ssDNA/SWNT-FET exposed to TMA vapor (black). Source-drain bias voltage is 100 mV.
Figure 2B:
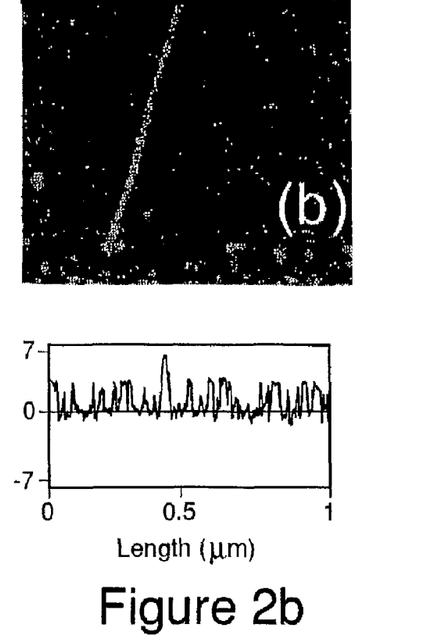
Figure 2C:
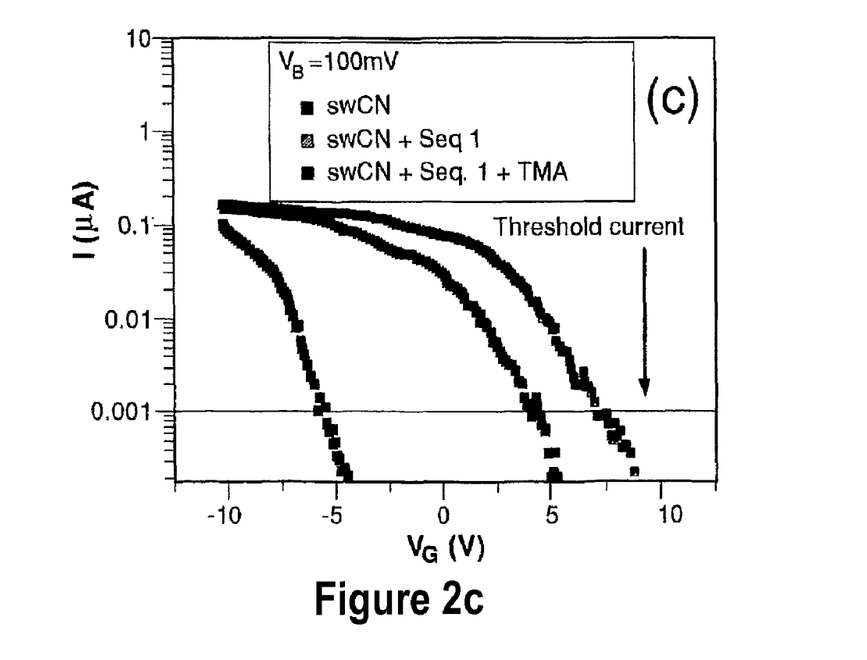

Statistical analysis of atomic force microscopy (AFM) images of the same tube before and after DNA application showed an increase in the nominal tube diameter from 5.4±0.1 nm to 7.2±0.2 nm, indicating formation of a nanoscale layer of ssDNA on the SWNT surface (FIG. 2a, b). For both of the sequences used, application of ssDNA caused the threshold value of $V_G$ for measurable conduction to decrease by 3-4 V (FIG. 2c). This corresponds to a hole density decrease of roughly 400/μm, assuming a backgate capacitance (25 aF/μm) that is typical for this device geometry. Furthermore, the "ON" state conductivity of the ssDNA/SWNT-FET was 10% lower than that of the bare device (FIG. 2c), suggesting weak carrier scattering by the molecular coating.

EXAMPLE 2 ssDNA-SWNT-FET Detection of Propionic Acid, Trimethylamiene, Methanol Dinitrotoluene, and Dimethyl Methylphosphonate The data below demonstrate that single walled carbon nanotubes coated with single-stranded DNA oligomers show conductance changes when target molecular species are applied to a chemical sensor described herein. The odor responses are different in sign and/or magnitude for different odors and the odor responses also depend on the base sequence of the DNA decorating the SWNTs. SWNTs were fabricated and arrayed for conductance measurements in an FET-like configuration.

Five odors were used with ssDNA-decorated sensor devices of the present invention to yield differential odor responses. These odors are:

Dinitrotoluene (DNT) is of interest because of its similarity to the explosive TNT, although DNT is not explosive. Similarly, dimethyl methylphosphonate (DMMP) is a non-lethal analogue of the nerve agent sarin.

A reservoir of saturated vapor of each odor was prepared and connected to a peristaltic pump and switching valve array so that the flow of room air directed over the device (0.1 ml/sec) could be electrically diverted to one of the odor reservoirs for a set time, after which the flow reverted to plain air. Odor pulses of 50 sec duration were used. The air or air/analyte mixture was directed towards the sample through a 2±0.1 mm diameter nozzle positioned 6±1 mm above the sample surface. For each analyte, it is estimated that the concentration delivered to the sample was about 3% of the appropriate saturated vapor pressure (Table 1). The source-drain current through the device $I_{SD}$ was measured as a function of gate voltage $V_G$ for a fixed bias voltage $V_B$. For each sample (both with and without DNA coating), it was found that $V_G=0$ was a region of large transconductance ($dI/dV_G$), where high sensitivity of the SWNT to environmental perturbations is expected. With the gate voltage set to $V_G=0V$, the current $I_{SD}$ was then monitored as the sample (SWNT or SWNT+DNA coating) was exposed to one of the three odors.

TABLE 1

Measured responses of SWNT devices to gaseous analytes.

| Odor | vapor pressure (Torr) | Est. conc. (ppm) | bare SWNT %ΔI/I | SWNT + ssDNA SEQ ID NO:. 1 %ΔI/I | SWNT + ssDNA SEQ ID NO: 2 %ΔI/I |
|---|---|---|---|---|---|
| Water | 17.5 | 700 | 0 ± 1 | 0 ± 1 | 0 ± 1 |
| Propionic acid | 4 | 150 | 0 ± 1 | +17 ± 2 | +8 ± 1 |
| TMA | 500 | 20000 | −9 ± 2 | −20 ± 2 | −30 ± 2 |
| Methanol | 100 | 4000 | 0 ± 1 | −12 ± 2 | −20 ± 2 |
| DMMP | 0.6 | 25 | 0 ± 1 | −14 ± 2 | −7 ± 2 |
| DNT | 1 | 40 | 0 ± 1 | −14 ± 4 | −4 ± 2 |

Estimated concentration corresponds to 3% of the saturation vapor pressure (www-.sciencestuff.com). Each quoted sensor response is based on measurements of 5-10 different devices. Uncertainties are the standard deviation of the mean.

Figure 3A:
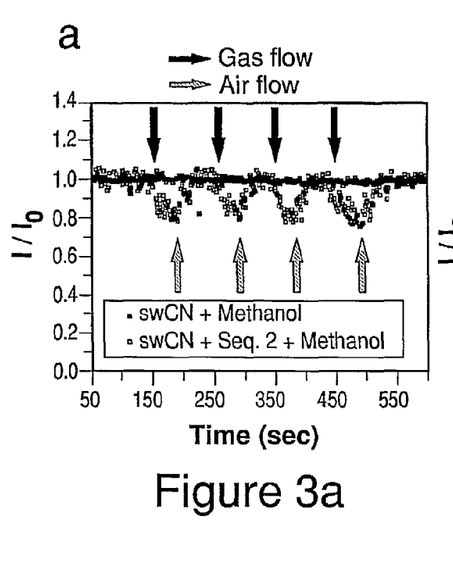
Figure 3B:
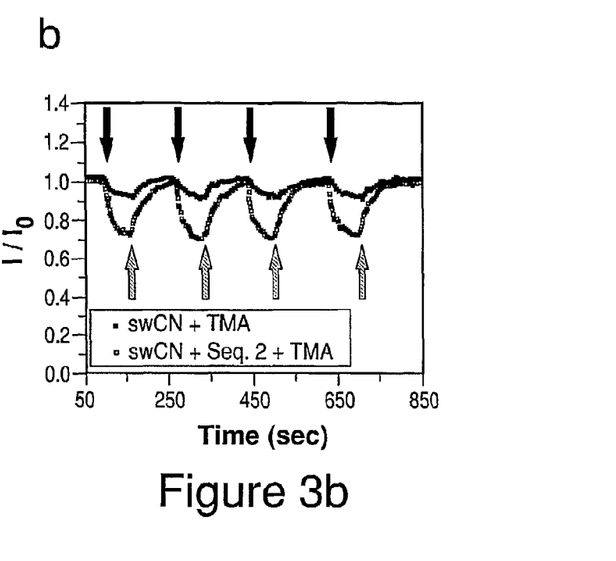
Figure 3C:
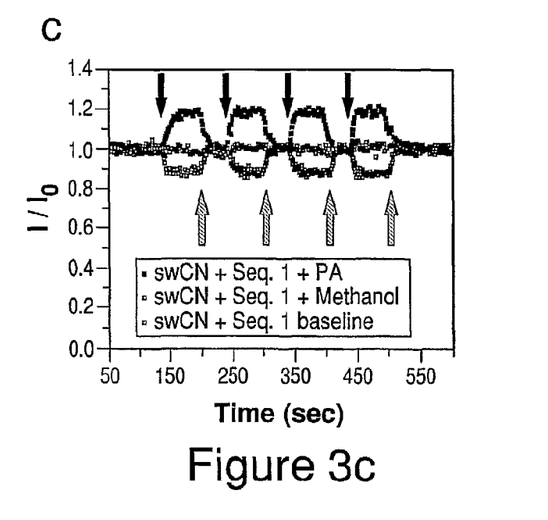

Responses of SWNT-FET devices with or without (bare) ssDNA functionalization were compared. It was observed that the bare SWNT (NT+TMA) does not respond to the odor analyte trimethylamine whereas a SWNT adsorbed to an oligonucleotide bearing SEQ ID NO:2 (NT+SEQ ID NO:2+TMA) yields clear responses to the trimethylamine analyte (FIG. 3b). Similarly, bare SWNT demonstrated minimal sensitivity to methanol (ΔI/I~1%), whereas SWNT functionalized with ssDNA having SEQ ID NO:2 showed a 20% decrease in transport current (FIG. 3a). These results indicate that ssDNA increases the binding affinity for methanol or trimethylamine to the device, thereby increasing the sensor response. Even when a bare SWNT sensor responds to a particular gas (ΔI/I=−10% on exposure to TMA, FIG. 3b), functionalization with ssDNA enhances the molecular affinity and associated response (ΔI/I=−30%). Additional experiments revealed that different odors elicit different current responses from ssDNA-functionalized SWNT-FET sensors. For example, the response to propionic acid of a device functionalized with ssDNA having SEQ ID NO: 1 differs in both sign and magnitude from the response to methanol (FIG. 3c). The data also demonstrate that a constant sensor response is maintained through multiple odor exposures.

Figure 4A:
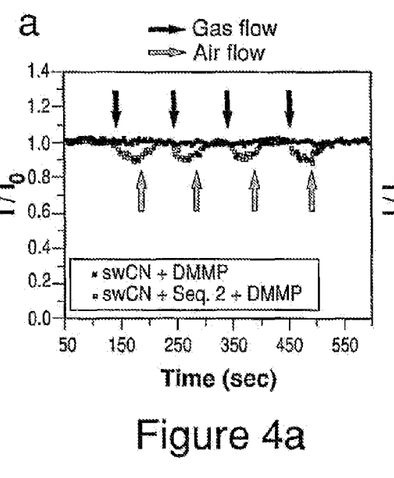
Figure 4B:
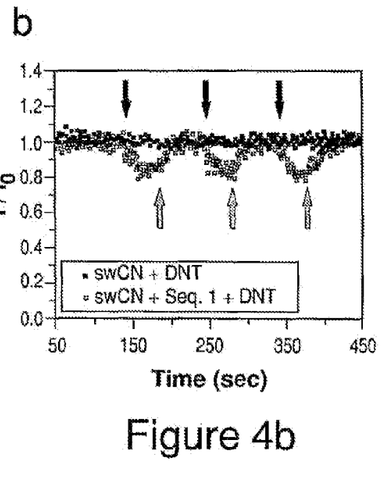

SWNT sensors functionally adsorbed to ssDNA having SEQ ID NO:2 were observed to be sensitive to both DMMP and DNT (FIG. 4a), whereas sensors functionally adsorbed to ssDNA having SEQ ID NO: 1 did not show a response to the DMMP odor analyte (FIG. 4b). Control experiments verified that the ssDNA-SWNT-FET sensor did not respond to dipropylene glycol, the solvent used for DNT. In addition, no response of the sensor to water vapor, a common background substance, was observed, regardless of whether the sensor was functionally attached to ssDNA having SEQ ID NO:1 or SEQ ID NO:2. The signal-to-noise levels of the experimental measurements depicted in FIG. 4 indicate that detection of volatile compounds with concentrations less than 1 ppm is possible. The DMMP concentration used in this experiment is estimated to be 25 ppm, and the observed response is distinct but modest (ΔI/I~−7% for ssDNA SEQ ID NO:1, and −14% for ssDNA SEQ ID NO:2). The results are summarized in Table 2. The results indicate that measured odor responses differ depending on both the sequence of the DNA strand decorating the SWNTs and the identity of the odor being applied.

TABLE 2

Comparison of SWNT response to various odor analytes.

| Gas | % ΔI/I for SWNT | % ΔI/I SWNT + ssDNA SEQ ID NO: 1 | % ΔI/I SWNT + ssDNA SEQ ID NO: 2 |
|---|---|---|---|
| Water | 0 | 0 | 0 |
| Propionic acid | 0 | +7 ± 2 | +10 ± 2 |
| TMA | −15 ± 1 | −8 ± 2* | −50 ± 2 |
| Methanol | 0 | −10 ± 2 | −30 ± 2 |
| DMMP | 0 | 0 | −10 ± 1 |
| DNT | 0 | 0 | −7 ± 2 |

The data shown are percent change in conductance. Uncertainties are standard deviation of the mean.
(*This sample showed no response to TMA before applying ssDNA having SEQ ID NO: 1).

The number of distinct ssDNA oligonucleotides that can be generated is extremely large. It is expected that an oligonucleotide can readily bind to SWNT via a pi-pi stacking interaction. Accordingly, it is possible to generate a large family of carbon nanotube-based sensors having distinct odor response characteristics, an important building block of "electronic nose" and "electronic tongue" systems.

As a test of response reproducibility, a SWNT device was exposed to 50 cycles of TMA and air exposure (odor and air pulses each 50 seconds in duration). The results demonstrated that the response of the device to the analyte was maintained within 5% even after 50 trials (data not shown). This indicates that the ssDNA-SWNT have a significant advantage over other detection devices in that the ssDNA sensor surface is not used up with each detection, and that the ssDNA-SWNT are thus self-regenerating, meaning that they reset after each detection, and remain viable for additional analyses. In contrast, other analytical devices are typically irreversibly bound to the analyte, meaning that the sensor must be regenerated for each subsequent analysis. Device-to-device variation in odor response was also observed to be small (Table 1). This excellent reproducibility observed for both a single device and across devices indicates very favorable prospects for quantitative modeling of individual devices and integrated systems.

In a few samples utilizing ssDNA having SEQ ID NO:2, a response to trimethylamine was observed before application of the DNA. This may be the result of some analytes perturbing the electronic structure of the SWNT wall directly. This perturbation may vary sample-to-sample. For these samples, the response was enhanced after applying the DNA solution, for example, a change from −15% to −50% in the transport current can be seen in Table 2. In general, bare SWNT-FET devices did not give odor responses while embodiments of the present invention gave differential odor responses depending on the identity of the odor and the sequence of bases in the ssDNA adsorbed to the SWNT. Note in FIG. 3 that the responses to propionic acid are different in sign and magnitude from the response to TMA.

EXAMPLE 3

Computer Simulations Showing the Possible Mechanism Behind Volatile Sensing Using ssDNA-Functionalized SWNTs All-atom molecular dynamics (MD) simulations including up to 50,000 water molecules were conducted to investigate adsorption of ssDNA onto SWNTs, and the results compared with observations from experiments utilizing two different ssDNA sequences (SEQ ID NOS: 1 and 2).

Computations were carried out on Tungsten, an Intel Xeon 3.0 GHz Dell Cluster, at the National Center for Supercomputing Applications. These have recently been shifted to a local 128-node cluster. The GROMACS9 software package is employed for the MD. Electrostatic interactions were calculated using the Particle Mesh Ewald10 method. Constant temperature and pressure conditions were imposed using the Berendson thermostat, and Parrinello-Rahman barostat, respectively. (Berendsen H J et al. (1984) J. Chem. Phys. 81:3684-90; and, Parrinello M et al. (1981) J. Appl. Phys. 52:7182-90.) The AMBER99 force field and SPC216 model were used for the ssDNA and water, respectively, due to their reliability and widespread use. An empirical potential for the SWNT was employed that uses a Morse potential for the bonds, a cosine potential for the angles, a Lennard-Jones potential for the van der Waals and steric interactions, and a harmonic potential for dihedral angles. These force fields have been used successfully to study the encapsulation of ssDNA in a SWNT (Gao H et al. (2004) Annu. Rev. Mater. Res. 34:123-50.)

AFM measurements indicate adsorption of a homogenous ssDNA layer on the SWNT with a thickness of approximately 1.8 nm. The observed sequence-dependence of sensor response to gaseous analytes suggests that ssDNA assumed a non-trivial secondary structure when adsorbed on the SWNT. Measurements of device current as a function of backgate voltage implied unambiguously that when ssDNA adsorbs on the SWNT, the electrostatic potential it produces at the surface of the SWNT is positive. Since ssDNA in aqueous solution is known to have a large linear charge that is negative, this last result is strongly counterintuitive. The fact that the maximum device current is decreases by ~10% implies that carrier scattering due to ssDNA adsorption is weak.

The results from the MD simulations are in agreement with the 3 experimental findings mentioned in the last paragraph. MD simulations (FIG. 5) utilizing ssDNA having SEQ ID NO: 1 adsorbing onto a SWNT showed formation of a molecular layer of 1.5 nm thickness, similar to the observed 1.8 nm. The simulations also revealed non-trivial secondary structure in the ssDNA that may have implications for sensor response to small molecule analytes. Preliminary analysis of the structure suggests it results from a competition between pi-pi stacking of ssDNA bases with the six-member carbon rings that form the nanotube sidewall ("tube stacking") and with neighboring bases along the ssDNA chain7 ("self stacking"). Intriguingly, it was observed that ssDNA sequences previously identified as superior for SWNT sorting (Zheng M et al., 2003) do not assume such a secondary structure. "Tube stacking" dominates in these sequences, and they lie almost completely flat against the SWNT sidewall (data not shown).

Figure 5A:
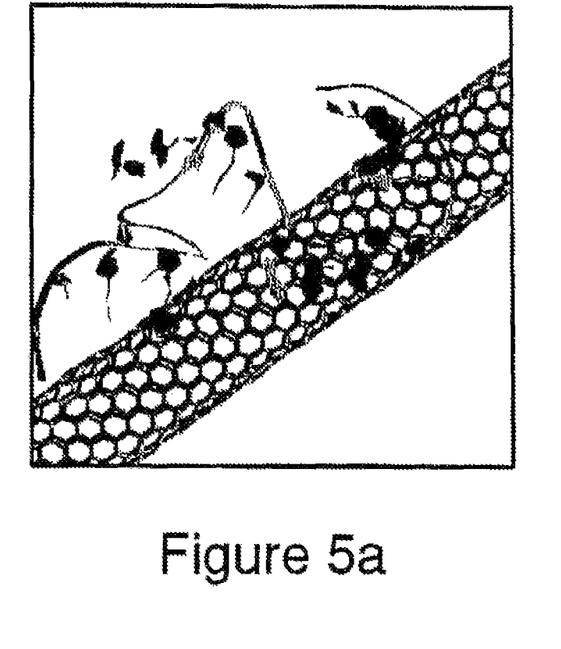
FIG. 5 shows the final state after 150 ps of a MD simulation that includes ssDNA, a SWNT, and 1000 water molecules (left panel). The ssDNA strand shown has SEQ ID NO: 1. The ssDNA has a secondary "pocket" structure that enhances its interaction with analyte molecules. The right panel shows electrostatic potential at the SWNT surface due to ssDNA molecules and cations, where the central region as shown has positive potential, and the end regions (left and right of center) as shown have negative potential. The dominant contribution to the potential in regions directly beneath the ssDNA molecules is from the counterions, making it positive, a counterintuitive result that agrees with experiment.
Figure 5B:
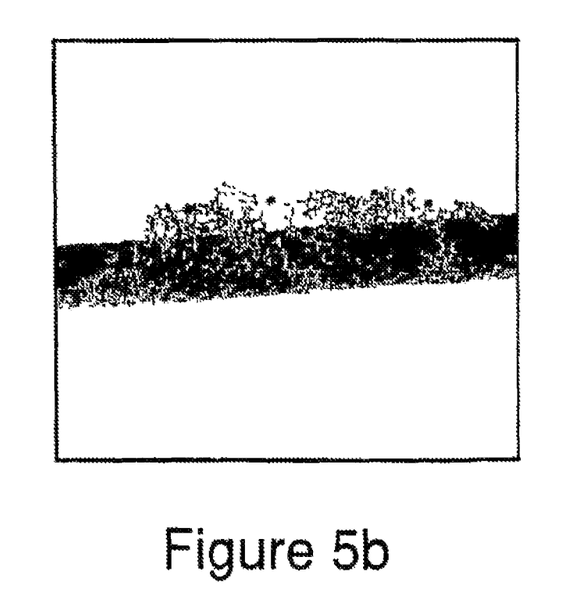

Using the final ssDNA conformation produced by the MD simulation described above, the electrostatic potential due to the combined effect of the ssDNA and its Na+ counterions at the surface of the SWNT was found to be positive, again in agreement with the experiment (FIG. 5). The simulation indicates that the positively charged counterions are not found randomly distributed around the negatively charged phosphate groups of the ssDNA backbone. Instead, they migrate preferentially to regions closer to the SWNT sidewall, and therefore dominate the electrostatic potential in this region.

The present invention is not limited to the embodiments described and exemplified above, but is capable of variation and modification within the scope of the appended claims.

What is claimed:

1. A chemical sensor comprising:
a semiconducting substrate capable of being operated as a backgate;
an insulating layer disposed on the semiconducting substrate;
source and drain electrodes disposed on the insulating layer;
at least one carbon nanotube in electrical contact with each of the source and drain electrodes,
wherein the carbon nanotube is in contact with the insulating layer; and
an oligonucleotide bound to the carbon nanotube via a pi-pi stacking interaction.

2. The chemical sensor of claim 1 wherein the nanotube is semiconducting.

3. The chemical sensor of claim 1, wherein the oligonucleotide is single stranded.

4. The chemical sensor of claim 3, wherein the oligonucleotide has SEQ ID NO:1 or SEQ ID NO:2.

5. The chemical sensor of claim 1 wherein the oligonucleotide is capable of interacting with at least one molecular species to affect the electric field local to the nanotube.

6. The chemical sensor of claim 4, wherein an altered current flow in the nanotube accompanies interaction of the molecular species with the oligonucleotide.

7. A chemical sensor comprising: a semiconducting substrate;
an insulating layer disposed on the substrate;
source and drain electrodes disposed on the insulating layer;
at least one carbon nanotube in contact with each of the source and drain electrodes; and
an oligonucleotide bound to the carbon nanotube via a pi-pi-stacking interaction;
the sensor being adapted to have a gate voltage applied to the substrate and a bias voltage applied between the source and drain electrodes; the carbon nanotube being capable of conducting current between the source and drain electrodes in response to an electric field local to the carbon nanotube.

8. The chemical sensor of claim 7 wherein said nanotube is semiconducting.

9. The chemical sensor of claim 7 wherein the oligonucleotide is single stranded.

10. The chemical sensor of claim 9, wherein the oligonucleotide has SEQ ID NO:1 or SEQ ID NO:2.

11. The chemical sensor of claim 7 wherein the oligonucleotide is capable of interacting with at least one molecular species to affect the electric field local to the nanotube.

12. The chemical sensor of claim 11 wherein an altered current flow in the nanotube accompanies interaction of the molecular species with the oligonucleotide.

13. A method of using a chemical sensor comprising: a semiconducting substrate;
an insulating layer disposed on the substrate;
source and drain electrodes disposed on the insulating layer;
at least one carbon nanotube in contact with each of the source and drain electrodes:
an oligonucleotide bound to the carbon nanotube via a pi-pi stacking interaction, comprising: contacting said sensor with an atmosphere sample and detecting the presence or absence of a volatile compound.

14. The method of claim 13 wherein said nanotube is semiconducting.

15. The method of claim 13 wherein the oligonucleotide is single stranded.

16. The method of claim 15, wherein the polynucleotide oligonucleotide has SEQ ID NO:1 or SEQ NO:2.

17. The method of claim 13 wherein the oligonucleotide is capable of interacting with at least one molecular species to affect the electric field local to the nanotube.

18. The method of claim 17 wherein an altered current flow in the nanotube accompanies interaction of the molecular species with the oligonucleotide.

19. A chemical sensor array comprising a plurality of sensors in accordance with claim 1 or claim 7.

20. The chemical sensor array of claim 19 wherein different sensors or sets of sensors are sensitive to a different molecule or molecular family or genus.

21. The chemical sensor array of claim 19 further comprising a data processing system.

22. The chemical sensor array of claim 21 wherein said data processing system further comprises a pattern recognition data processing system.

23. A chemical sensor array comprising a plurality of sensors in accordance with claim 7.

24. The chemical sensor array of claim 23 wherein different sensors or sets of sensors are sensitive to a different molecule or molecular family or genus.

25. The chemical sensor array of claim 23 further comprising a data processing system.

26. The chemical sensor array of claim 25 wherein said data processing system further comprises a pattern recognition data processing system.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 1
gagtctgtgg aggaggtagt c                                              21

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 2
cttctgtctt gatgtttgtc aaac                                           24